United States Patent
Chang et al.

(10) Patent No.: US 6,861,533 B2
(45) Date of Patent: Mar. 1, 2005

(54) SOLUTION PHASE SYTHESIS OF ARYLBENZOXAZOLES

(75) Inventors: Junbiao Chang, Zhengzhou (CN); Shifeng Pan, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 10/300,336

(22) Filed: Nov. 19, 2002

(65) Prior Publication Data

US 2003/0148387 A1 Aug. 7, 2003

Related U.S. Application Data

(60) Provisional application No. 60/333,241, filed on Nov. 23, 2001.

(51) Int. Cl.$^7$ ............................................. C07D 263/56
(52) U.S. Cl. ...................................... 548/224; 548/217
(58) Field of Search ................................. 548/217, 224

(56) References Cited

FOREIGN PATENT DOCUMENTS

| EP | 0806419 A1 | 11/1997 |
|---|---|---|
| WO | WO 98/46594 A1 | 10/1998 |

OTHER PUBLICATIONS

Varma, R. S.; Saini, R. K.; Prakash, O. "Hypervalent Iodine Oxidation of Phenolic Schiff's Bases: Synthesis of 2–Arylbenzoxazoles" Tetrahedron Letters, 1997, 38(15), 2621–2622.*

Smith, M. B.; March, J. March's Advanced Organic Chemistry: Reactions, Mechanisms, and Structure. New York: John Wiley & Sons, Inc. 2001, p. 1511.*

Li, P.; Gi, H.–J.; Sun, L.; Zhao, K. "Oxidative Conversion of Isoxazolidines to Isoxazolines" J. Org. Chem. 1998, 63, 366–369.*

Sate et al., *The Journal of Antibiotics*, 54:1: 102–104 (2001).

Temiz et al., *II Farmaco*, 53: 337–341 (1998).

DeLuca et al., *Tetrahedron Letters*, 38:2: 199–202 (1997).

Wang et al., *Tetrahedron Letters*, 38:37: 6529–6532 (1997).

* cited by examiner

*Primary Examiner*—Bennett Celsa
*Assistant Examiner*—Jon D. Epperson
(74) *Attorney, Agent, or Firm*—Morgan, Lewis & Bockius LLP

(57) ABSTRACT

This invention provides methods for the solution-phase synthesis of arylbenzoxazoles. The methods involve condensation of aminophenols with benzaldehydes to form a Schiff base. The Schiff base is then induced to undergo oxidative cyclization in the presence of DDQ. The resulting arylbenzoxazoles can be separated from the reduced DDQ byproduct by treatment of reaction mixture with a strongly basic ion exchange resin.

6 Claims, No Drawings

SOLUTION PHASE SYTHESIS OF ARYLBENZOXAZOLES

CROSS-REFERENCE TO RELATED APPLICATIONS

This is a non-provisional filing of U.S. Provisional Patent Application No. 60/333,241, filed on Nov. 23, 2001, the disclosure of which is incorporated herein by reference in its entirety for all purposes.

BACKGROUND OF THE INVENTION

1. Field of the Invention

This invention pertains to the field of solution phase synthesis of oxazoles, particularly 2-arylbenzoxazoles.

2. Background

Oxazoles are a class of pharmaceutically active compounds. Aryloxazoles such as the 2-Arylbenzoxazoles possess the important biaryl pharmacophore and they exhibit a variety of biological activities, including antimicrobial and antitumor properties. For example, a 2-arylbenzoxazole, AJI9561, was recently isolated as a cytotoxic metabolite from the extract of Streptomyces sp. (Sato et al., J. Antibiot. 2001, 54, 102). For other recent examples, see, Temiz et al., Farmaco 1998 53, 337; Aotsuka et al., PCT Int. Appl. WO 98 46,594 1998; Sato et al., Eur. Pat. Appl. EP 806,419 1997; and Deluca et al., Tetrahedron Lett. 1997, 38, 199.

The two most popular methods for synthesizing 2-substituted benzoxazoles are the coupling of carboxylic acids with 2-aminophenols by dehydration catalyzed by a strong acid (Terashima et al., Synthesis 1982, 1484 and references cited therein), and the oxidative cyclization of phenolic Schiff bases, derived from the condensation of 2-aminophenols and aldehydes. The oxidation is effected using various oxidants, such as $PhI(OAc)_2$ (Varma et al., Tetrahedron Lett. 1997, 38, 2621), $Mn(OAc)_3$ (Varma et al., J. Heterocyclic Chem. 1998, 35, 1539), $Th^+ClO_4^-$(Park et al., Tetrahedron Lett. 1996, 37, 8869), $Ba(MnO_4)_2$ (Srivastava et al., Synth. Commun. 1988, 18, 1537), $NiO_2$ (Nakagawa et al., Chem. Pharm. Bull. 1964, 12, 1135) and $Pb(OAc)_4$ (Stephens et al., J. Chem. Soc. 1949, 2971). The first method is of use for making large quantities of pharmaceutical intermediates but typically requires activation of the carboxylic acid under strongly acidic conditions at high temperature. Thus, this method is inappropriate for substrates that include heat-sensitive or acid-labile moieties. The second method generally involves the use of transition metals. The metal byproducts must be removed from the product by filtration or aqueous treatment.

Recently, both solution and solid-phase methods for the synthesis of combinatorial libraries have gained tremendous popularity (see, Thompson et al., Chem. Rev. 1996, 96, 555; Balkenhohl, Angew. Chem. Int. Ed. Engl. 1996, 35, 2288; Hermkens et al., Tetrahedron 1996, 52, 4527; Baldino, C. M. J. Comb. Chem. 2000, 2, 89 and references cited therein). The preparation of compound libraries requires the development of simple and high yielding methods for both the synthesis and purification of the library compounds. Although there have been several reports describing the solid-phase synthesis of benzoxazoles (Wanget al., Tetrahedron Lett. 1997, 38, 6529) there has yet to appear a description of solution-phase libraries of benzoxazoles, presumably due to the lack of any robust procedure for synthesis and purification of these compounds. Accordingly, a need exists for solution-phase synthesis of benzoxazoles. The present invention fulfills this and other needs.

SUMMARY OF THE INVENTION

The present invention provides methods for the synthesis of an oxazole. The method of the invention is exemplified by the synthesis of arylbenzoxazoles, particularly 2-arylbenzoxazoles. An exemplary method involves condensing an aminophenol and an aromatic aldehyde to form a Schiff base. The Schiff base is contacted with an oxidizing agent such as 2,3-dichloro-5,6-dicyano-1,4-benzoquinone (DDQ) to form an arylbenzoxazole. The method of the invention can be performed in solution phase. Should purification of the final product be desired, in some embodiments, the arylbenzoxazole is readily separated from impurities using ion exchange chromatography.

Also provided by the invention are methods for preparing a combinatorial library of oxazoles, particularly arylbenzoxazoles. The methods involve condensing each member of a population of aminophenols with each member of a library of aromatic aldehyde to form a combinatorial library of Schiff bases. The library of Schiff bases are contacted with an oxidizing agent such as 2,3-dichloro-5,6-dicyano-1,4-benzoquinone (DDQ) to form an arylbenzoxazole.

The present invention provides a method for preparing oxazoles. The one-pot procedure is mild and efficient, allowing for the presence of diverse substituents on both the aminophenol and aromatic aldehyde cores. Moreover, the combination of the present method and basic ion exchange purification of the product allows for the facile preparation of oxazole combinatorial libraries. The method described herein is the first example of benzoxazole library synthesis by a solution-phase strategy.

Additional objects, embodiments and advantages of the present invention are apparent from the detailed description below.

DETAILED DESCRIPTION OF THE INVENTION AND THE PREFERRED EMBODIMENTS

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 to 24 carbon atoms being preferred in the present invention. A "lower alkyl" or "lower alkylene" is a shorter chain alkyl or alkylene group, generally having eight or fewer carbon atoms, preferably four or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "halo" or "halogen," by themselves or as part of another substituent, mean, unless otherwise stated, a fluorine, chlorine, bromine, or iodine atom.

The term "aryl," employed alone or in combination with other terms (e.g., aryloxy, arylthioxy, arylalkyl) means, unless otherwise stated, an aromatic substituent that is a single ring or multiple rings (up to three rings) which are fused together or linked covalently. The term "heteroaryl" refers to those aryl groups in which at least one of the rings contains from one to four heteroatoms selected from N, O, and S, wherein the nitrogen and sulfur atoms are optionally oxidized, and the nitrogen atom(s) are optionally quaternized. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 2-pyridyl, 2-pyrimidyl, 5-benzothiazolyl, purinyl, 2-benzimidazolyl, 5-indolyl, 1-isoquinolyl, 2-quinoxalinyl, 3-quinolyl, and the like. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene and heteroalkylene) can be a variety of groups selected from: —OR', =O, =NR', =N—OR', —NR'R", —SR', -halogen, —SiR'R"R''', —OC(O)R', —CO$_2$R', —CONR'R", —OC(O)NR'R", —NR"C(O)R', —NR"C(O)NR'R''', —NR"C(O)$_2$R', —NHC(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. Preferably, substituted alkyl groups will have from one to six independently selected substituents, more preferably from one to four independently selected substituents, most preferably from one to three independently selected substituents. In the substituents listed above, R', R" and R''' each independently refer to hydrogen, substituted or unsubstituted alkyl and heteroalkyl, substituted or unsubstituted aryl, alkoxy or thioalkoxy groups, or arylalkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: -halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NR"C(O)NR'R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R' and R" are independently selected from hydrogen, (C$_1$-C$_8$)alkyl and heteroalkyl, unsubstituted aryl, (unsubstituted aryl)-(C$_1$-C$_4$)alkyl, and (unsubstituted aryl) oxy-(C$_1$-C$_4$)alkyl. Preferably, substituted aryl groups will have from one to four independently selected substituents, more preferably from one to three independently selected substituents, most preferably from one to two independently selected substituents.

As used herein, the term "heteroatom" is meant to include oxygen (O), nitrogen (N), sulfur (S), boron (B) and silicon (Si).

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base, an acid or an anion exchange medium and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The Methods

The present invention provides methods for solution-phase synthesis of oxazoles and oxazole libraries. The methods involve the formation of Schiff bases by the condensation of an aldehyde with an aminophenol. The Schiff base is contacted with an oxidizing agent, such as 2,3-dichloro-5,6-dicyano-1,4-benzoquinone (DDQ), leading to the oxidative cyclization of the phenolic Schiff base to produce an oxazole.

In an exemplary embodiment, the invention provides methods for preparing arylbenzoxazoles. In this embodiment, the phenol is preferably a substituted or unsubstituted 2-aminophenol and the aldehyde is a substituted or unsubstituted benzaldehyde.

The present solution-phase approach is an attractive choice for preparing oxazoles, because the reactions are high yielding and generate byproducts that are readily removed from the product. Schiff base formation between aminophenols and aldehydes generates only water as a byproduct and conversion of the Schiff base to the final products is achieved by the appropriate selection of oxidants. Those of skill will appreciate that an array of oxidants are of use to cyclize the Schiff base to the oxazole.

In an exemplary embodiment, the method of the invention makes use of 2,3-dichloro-5,6-dicyano-1,4-benzoquinone (DDQ) as an oxidant. DDQ is a versatile reagent for the oxidation of alcohols and selected amino groups. Moreover, 4,5-dichloro-3,6-dihydroxy-phthalonitrile (DDP), the reduced product of DDQ, is easily removed from the reaction mixture by, for example, basic ion-exchange resins, thereby enabling the solution-phase synthesis of the desired library. DDQ has used in the synthesis of benzoimidazoles from corresponding o-phenylenediamines and aldehydes (Vanden Eynde et al., *Tetrahedron* 1995, 51, 5813. Li and co-workers have also reported the DDQ oxidation of hydroxylamine groups to the corresponding isoxazolines (Li et al., *Org. Chem.* 1998, 63, 366).

With reference to Scheme 1, 2-arylbenzoxazole 4 results from the treatment of the phenolic Schiff base 3 with DDQ. The Schiff base is formed via the condensation of 2-aminophenol 1 and aromatic aldehyde 2 in methanol.

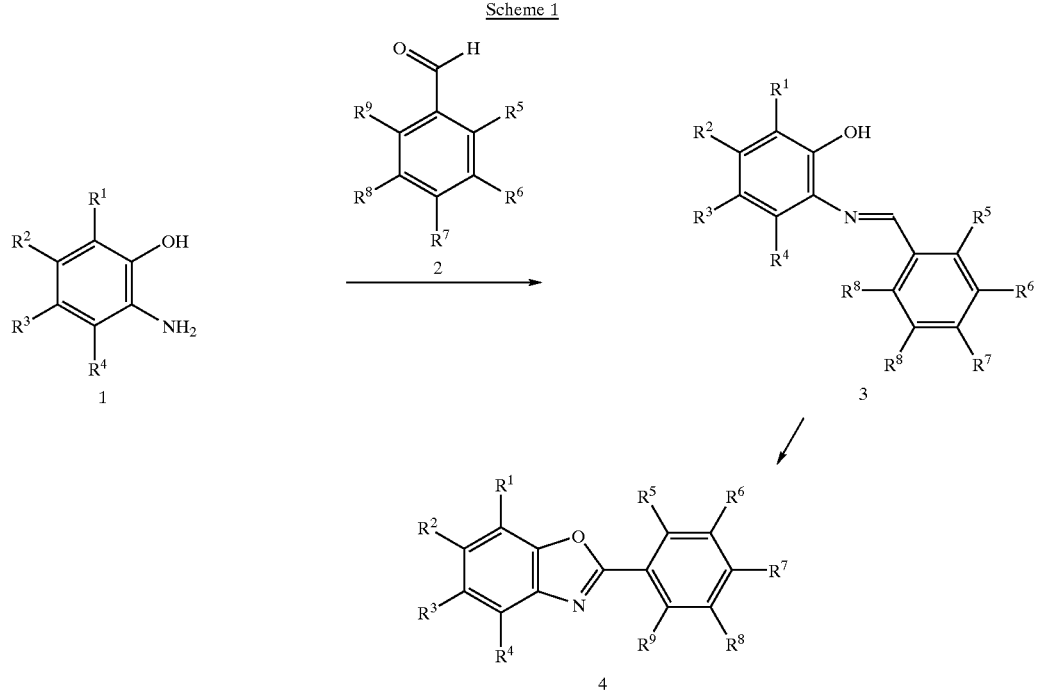

Scheme 1

Each of the R groups in the scheme above, are independently selected from the aryl substituents set forth in the definitions section hereinabove. Exemplary groups include H, $NO_2$, halogen, alkoxy, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^1$, $R^2$, $R^3$, and $R^4$ are optionally joined to form a 4- to 7-member ring system.

Libraries

Also within the scope of the present invention are methods of preparing libraries of oxazoles utilizing the synthetic methods of the invention. The libraries preferably include at least 10 compounds, more preferably at least 100 compounds, even more preferably at least 1000 compounds and still more preferably at least 100,000 compounds.

Thus, in a second aspect, the invention provides method of synthesizing a combinatorial library of arylbenzoxazole compounds or pharmaceutically acceptable salts thereof. The method includes condensing each member of a population of aminophenols with each member of a library of aromatic aldehydes to form a combinatorial library of Schiff bases. The library of Schiff bases is converted to the library of oxazoles by contacting each member of the combinatorial library of Schiff bases with an oxidizing agent.

The synthesis and screening of chemical libraries to identify compounds having useful biological and material properties is now a common practice. Illustrative of the many different types of libraries that have been prepared are libraries including collections of oligonucleotides, oligopeptides, and small or large molecular weight organic or inorganic molecules. See, Moran et al., PCT Publication WO 97/35198, published Sep. 25, 1997; Baindur et al., PCT Publication WO 96/40732, published Dec. 19, 1996; Gallop et al., *J. Med. Chem.* 37: 1233–51, 1994.

Parallel, or combinatorial, synthesis has as its primary objective the generation of a library of diverse molecules which all share a common feature, referred to throughout this description as a scaffold. By substituting different moieties at each of the variable parts of the scaffold molecule, the amount of space explorable in a library grows. Theories and modern medicinal chemistry advocate the concept of occupied space as a key factor in determining the efficacy of a given compound against a given biological target. By creating a diverse library of molecules, which explores a large percentage of the targeted space, the odds of developing a highly efficacious lead compound increase dramatically.

Parallel synthesis of "small" molecules (non-oligomers with a molecular weight of 200–1000) was rarely attempted prior to 1990. See, for example, Camps et al., *Annals de Quimica,* 70: 848, 1990. In contrast to the situation in the early 1990s, many methods of introducing molecular structural diversity into libraries of compounds are now known in the art and are appropriate for use in the present invention (see, for example, Combinatorial Chemistry and Molecular Diversity in Drug Discovery, Gordon et al. (eds.), Wiley-Liss, New York, 1998.

In another exemplary embodiment, the library of the invention is provided with a means by which a library member (e.g., peptide sequence) can be resolved from the other library members. Many such means for deconvoluting a library of compounds are known in the art, including, for example, the use of tags, positional libraries, and ordered arrays. In an exemplary embodiment, the library prepared by a method of the invention has a first member located at a first region of a substrate and a second member located at a second region of a substrate.

Libraries in a positional or an ordered array motif are readily prepared using the methods provided herein. Such libraries permit the identification of compounds that are associated with zones of activity located during screening the library. Specifically, the library can be ordered so that the position of the compound on the array corresponds to the identity of the compound. Thus, once an assay has been carried out, and the position on the array determined for an active compound, the identity of that compound can be easily ascertained.

In another exemplary embodiment, the present invention provides a library in a microarray format comprising n compounds distributed over n regions of a substrate. Preferably, each of the n compounds is a different compound. In a still further embodiment, the n compounds are patterned on the substrate in a manner that allows the identity of the compound at each of the n locations to be ascertained. The microarray is patterned from essentially any type of oxazole compound prepared by a method of the invention.

A variety of methods are currently available for making arrays of molecules, such as arrays of antibodies, nucleic acid molecules, proteins, peptides and other small molecules. One method for making ordered arrays of compounds on a porous membrane is a "dot blot" approach. In this method, a vacuum manifold transfers a plurality, e.g., 96, aqueous samples of a compound from 3 millimeter diameter wells to a porous membrane. A common variant of this procedure is a "slot-blot" method in which the wells have highly-elongated oval shapes.

If it is desired to immobilize the compound on the substrate, e.g., a porous membrane, methods such as baking the membrane or exposing it to UV radiation are known in the art. This is a manual procedure practical for making one array at a time and usually limited to 96 samples per array.

A more efficient technique employed for making ordered arrays of compounds uses an array of pins dipped into the wells, e.g., the 96 wells of a microtitre plate, for transferring an array of samples to a substrate, such as a porous membrane. One array includes pins that are designed to spot a membrane in a staggered fashion, for creating an array of 9216 spots in a 22×22 cm area. See, Lehrach, et al., Hybridization Fingerprinting in Genome Mapping and Sequencing, Genome Analysis, Vol. 1, Davies et al, Eds., Cold Springs Harbor Press, pp. 39–81 (1990).

An alternate method of creating ordered arrays of compounds is described by Pirrung et al. (U.S. Pat. No. 5,143,854, issued 1992), and also by Fodor et al., (*Science,* 251: 767–773, 1991). The method involves synthesizing different compounds at different discrete regions of a substrate. A related method is described by Southern et al. (*Genomics,* 13: 1008–1017, 1992).

Khrapko, et al., *DNA Sequence,* 1: 375–388, 1991 describes a method of making a compound matrix by spotting the compound onto a thin layer of polyacrylamide. The spotting is done manually with a micropipette.

When the library is associated with a substrate, the substrate can also be patterned using techniques such as photolithography (Kleinfield et al., *J. Neurosci.* 8: 4098–120 1998), photoetching, chemical etching and microcontact printing (Kumar et al., *Langmuir* 10: 1498–511, 1994). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y.; Whitesides, G., *J. Am. Chem. Soc.* 117: 3274–75, 1995. Similarly, using photolithography, patterns with features as small as 1 μm have been produced. See, Hickman et al., *J. Vac. Sci. Technol.* 12: 607–16, 1994.

The pattern can be printed directly onto the substrate or, alternatively, a "lift off" technique can be utilized. In the lift off technique, a patterned resist is laid onto the substrate, a compound is laid down in those areas not covered by the resist and the resist is subsequently removed. Appropriate resists are known to those of skill in the art. See, for example, Kleinfield et al., *J. Neurosci.* 8: 4098–120, 1998. Following removal of the photoresist, a second compound, having a structure different from the first compound can be bonded to the substrate on those areas initially covered by the resist. Using this technique, substrates with patterns having regions of different chemical characteristics can be produced. For example, a pattern consisting array of adjacent wells is created by varying the hydrophobicity/ hydrophilicity, charge or other chemical characteristics of the pattern constituents. In one embodiment, hydrophilic compounds can be confined to individual wells by patterning walls using hydrophobic materials. Similar substrate configurations are accessible through microprinting a layer with the desired characteristics directly onto the substrate. See, Mrkish et al., *Ann. Rev. Biophys. Biomol. Struct.* 25: 55–78, 1996.

Kits

In another aspect, the present invention provides kits containing one or more component of use in practicing the methods of the invention and directions for using the component to prepare an oxazole and/or a library of oxazoles. Other formats for kits will be apparent to those of skill in the art and are within the scope of the present invention.

The following examples are offered to illustrate, but not to limit the present invention.

EXAMPLES

Example 1 provides an exemplary synthesis of an oxazole using a method of the invention. Example 2 sets forth an exemplary synthesis of a solution phase oxazole library using the method of the invention.

Example 1

A representative experimental procedure is as follows: To a solution of 2-aminophenol (0.109 g, 1.0 mmol) in MeOH (5 mL) was added p-anisaldehyde (0.136 g, 1.0 mmol). The resulting mixture was heated at 45° C. for 12 h. After concentration under reduced pressure, the residue was dissolved in $CH_2Cl_2$ (10 mL) and DDQ (0.250 g, 1.1 mmol) was then added. After stirring at room temperature for 30 min, the resulting mixture was diluted with additional $CH_2Cl_2$ (10 mL) and washed sequentially with saturated $Na_2CO_3$ (10 mL×2) and brine (10 mL). The organic layer was dried over anhydrous $Na_2SO_4$. After evaporation, the crude was purified by flash column chromatography (10% EtOAc in hexane) to afford the desired product (0.187 g, 83%). $^1H$ NMR (400 MHz, $CDCl_3$) δ 3.91 (s, 3H), 7.05 (d, 2H, J=9.0 Hz), 7.34 (m, 2H), 7.58 (d, 1H, 9.1 Hz), 7.76 (d, 1H, 9.0 Hz), 8.22 (d, 2H, 9.0 Hz). $^{13}C$ NMR (400 MHz, $CDCl_3$) δ 55.9, 110.8, 114.8, 120.0, 120.1, 124.8, 125.0, 129.8, 142.7, 152.6, 162.8, 164.0.

The results of performing the reaction cycle set forth above on exemplary substrates are set forth in Table 1. The desired oxidation presumably occurred after the cyclization of phenolic Schiff bases with the phenol hydroxy moiety to give the corresponding oxazolines. The 2-aminophenols with electron-withdrawing groups, which were predicted to be less reactive toward aldehydes, gave comparable results (entries 5–6, 10–11). For a nitro compound, higher reaction temperatures (reflux in ethanol) were utilized for the formation of Schiff base, providing the final products in excellent yields. This method employs aldehydes with both electron-donating (entries 3, 6, and 11) and electron-withdrawing groups (entries 2, 5 and 8). In addition, heterocyclic aldehydes can also be used for efficient preparation of various 2-heterocyclic substituted benzoxazoles (entries 4, and 11–12). These results have shown that DDQ is an efficient oxidation agent for the one-pot synthesis of benzoxazole-containing biaryl structures.

TABLE 1

| Entry | Product | Isolation A % Yield[a] | Isolation B % Yield[b] | % Purity[c] |
|---|---|---|---|---|
| 1 | 2-phenylbenzoxazole | 93 | 75 | 94 |
| 2 | 2-(4-chlorophenyl)benzoxazole | 95 | 84 | 94 |
| 3 | 2-(4-methoxyphenyl)benzoxazole | 83 | 63 | 87 |
| 4 | 2-(3-pyridyl)benzoxazole | 74 | 57 | 97 |

TABLE 1-continued

| Entry | Product | Isolation A % Yield[a] | Isolation B % Yield[b] | Isolation B % Purity[c] |
|---|---|---|---|---|
| 5[d] | 6-nitro-2-(4-chlorophenyl)benzoxazole | 92 | 85 | >99 |
| 6[d] | 6-nitro-2-(4-methoxyphenyl)benzoxazole | 91 | 82 | >99 |
| 7 | 5-methyl-2-phenylbenzoxazole | 89 | 89 | 97 |
| 8 | 5-methyl-2-(4-chlorophenyl)benzoxazole | 96 | 90 | 91 |
| 9 | 5-methyl-2-(2-thienyl)benzoxazole | 94 | 85 | 97 |
| 10 | 5-chloro-2-(2-furyl)benzoxazole | 81 | 55 | 86 |
| 11 | 5-chloro-2-(4-methoxyphenyl)benzoxazole | 82 | 76 | >99 |

[a]Isolated yields by flash column chromatography;
[b]Crude yields after ion-exchange resin treatment;
[c]HPLC purities of Isolation B were determined by integration of peak areas at 255 nm without calibration;
[d]Refluxing in ethanol for the formation of 3.

Example 2

A library of oxazoles was prepared using the general method set forth above. One prerequisite is to remove the DDP in a high throughput format. Among various purification methods available for solution-phase combinatorial synthesis, the treatment of reaction solutions with ion exchange resins has proven effective in the removal of some acidic or basic byproducts (For examples, see, Kulkarni et al., *Angew. Chem. Int. Ed. Engl.* 1997, 36, 2454; and Siegel et al., *Tetrahedron Lett.* 1997, 38, 3357), and there is a recent report demonstrating the applicability of ion exchange to a 96-well format (Bookser et al., *J. Comb. Chem.* 2001, 3, 205).

Basic ion-exchange resins were used to neutralize and absorb acidic DDP. Amberlite® IRA-900, which is a macroreticular resin with benzyltrialkylammonium functionality, proved to be the highly efficient in this respect. The results are summarized in Table 1 as Isolation B. The material loss, as indicated by crude yields in Table 1, was mainly due to the binding of the product by the resin.

Amberlite® IRA-900 (4 g) was freshly washed with methanol and used for the purification of each reaction on a 0.2 mmol scale, providing highly pure oxazole products. The ratios of reactant amounts was controlled, thus, there was no need to use a polymer-bound scavenger resin for removing DDQ from the reaction solutions (Deegan et al., *Tetrahedron Lett.* 1997, 38, 4973).

A 352-member library was then prepared by this solution-phase strategy. Thus, 82-aminophenols and 44 arylaldehydes were prepared as 0.1 M stock solutions in methanol. Aliquots of the stock solutions were then mixed in four 2 mL 96 (8×12) deep-well plates (0.2 mL of 2-aminophenol and 0.2 mL of aldehyde in each well). The loaded plates were heated in an oven at 45° C. for 12 hours. The methanol was removed using a plate rotary evaporator. The resulting residue in each well was redissolved in 0.2 mL of 1,2-dichloroethane (DCE). The DCE solutions were treated with 0.2 mL of 0.1 M DDQ in 10% THF to improve the solubility of DDQ. The reaction plates were agitated at room temperature for 2 hours before the solutions were transferred to filter bottom plates loaded with 0.4 g of freshly washed (MeOH) and dried Amberlite® IRA-900 in each well. DCE (0.4 mL) was added to each well. The plates were clamped and slowly rotated for 2 hours before filtering the solution into collection plates. The higher freezing temperature of DCE allowed the reaction solutions to be frozen so that possible leakage during the transfer was avoided. The final removal of solvents using a plate rotary evaporator gave the desired compounds in the collection plates.

The library was characterized by LC-MS. The purity of the individual compounds was determined by LC integration without calibration. 73% of the library showed purity greater than 80%. Only 9% of the compounds had purities less than 50%.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of synthesizing an arylbenzoxazole or a pharmaceutically acceptable salt thereof, the method comprising:
   (a) condensing an aminophenol and an aromatic aldehyde to form a Schiff base; and
   (b) contacting the Schiff base with an oxidizing agent, wherein the oxidizing agent is 2,3-dichloro-5,6-dicyano-1,4-benzoquinone (DDQ), thereby forming the arylbenzoxazole.

2. The method of claim 1, wherein the aminophenol is a 2-aminophenol.

3. The method according to claim 2, wherein said 2-aminophenol has the formula:

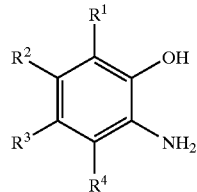

wherein $R^1$, $R^2$, $R^3$ and $R^4$ are members independently selected from H, $NO_2$, halogen, alkoxy, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^1$, $R^2$, $R^3$, and $R^4$ are optionally joined to form a 4- to 7-member ring system.

4. The method according to claim 1, wherein the aromatic aldehyde has the formula:

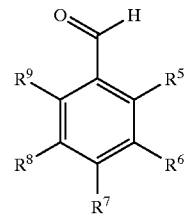

wherein $R^5$, $R^6$, $R^7$, $R^8$ and $R^9$ are members independently selected from H, $NO_2$, halogen, alkoxy, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^5$, $R^6$, $R^7$, $R^8$ and $R^9$ are optionally joined to form a 4- to 7-member ring system.

5. The method of claim 1, further comprising:
   (c) purifying the arylbenzoxazole by ion exchange chromatography.

6. The method of claim 1, wherein the method is performed in solution phase.

* * * * *